(12) United States Patent
Noda et al.

(10) Patent No.: US 10,314,558 B2
(45) Date of Patent: Jun. 11, 2019

(54) IMAGE PROCESSING APPARATUS, IMAGE PROCESSING SYSTEM, IMAGE PROCESSING METHOD, AND RECORDING MEDIUM

(71) Applicant: CANON KABUSHIKI KAISHA, Tokyo (JP)

(72) Inventors: Takeshi Noda, Ebina (JP); Yukari Nakashoji, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 544 days.

(21) Appl. No.: 15/052,486

(22) Filed: Feb. 24, 2016

(65) Prior Publication Data

US 2016/0296192 A1 Oct. 13, 2016

(30) Foreign Application Priority Data

Apr. 13, 2015 (JP) .................................. 2015-082094
Jun. 30, 2015 (JP) .................................. 2015-132180

(51) Int. Cl.
*A61B 6/00* (2006.01)
*G06F 19/00* (2018.01)
(Continued)

(52) U.S. Cl.
CPC .......... *A61B 6/5282* (2013.01); *G06F 19/321* (2013.01); *G06T 11/005* (2013.01); *A61B 6/032* (2013.01)

(58) Field of Classification Search
None
See application file for complete search history.

(56) References Cited

U.S. PATENT DOCUMENTS

2004/0202360 A1* 10/2004 Besson ................... G06T 5/008
382/131
2007/0086560 A1* 4/2007 Kia ....................... A61B 6/5282
378/7
(Continued)

FOREIGN PATENT DOCUMENTS

EP 2009592 A2 12/2008
JP 2010-188113 A 9/2010
(Continued)

OTHER PUBLICATIONS

Harry Ingleby, et al., "Fast Analytical Scatter Estimation Using Graphics Processing Units," Journal of X-Ray Science and Technology IOS Press Netherlands vol. 23, No. 2, Feb. 2015, pp. 119-133.

*Primary Examiner* — Matthew C Bella
*Assistant Examiner* — Brian D Shin
(74) *Attorney, Agent, or Firm* — Canon U.S.A., Inc. IP Division

(57) ABSTRACT

An image processing apparatus acquires a radiation image captured by irradiating an object with a radiation from a radiation source, estimates a scattered radiation image included in the acquired radiation image, and outputs a corrected image obtained by reducing the scattered radiation image from the acquired radiation image. The image processing apparatus estimates the scattered radiation image by applying a scattered radiation model for obtaining a scattered radiation component to the acquired radiation image based on a specific frequency component of an output of a first function and a specific frequency component of an output of a second function different from the first function.

29 Claims, 9 Drawing Sheets

(51) Int. Cl.
*G06T 11/00* (2006.01)
*A61B 6/03* (2006.01)

(56) References Cited

U.S. PATENT DOCUMENTS

| | | | | |
|---|---|---|---|---|
| 2009/0290682 A1* | 11/2009 | Star-Lack | ............ | G06T 11/005 378/87 |
| 2010/0046822 A1* | 2/2010 | Li | ........................... | A61B 6/00 382/132 |
| 2010/0208870 A1 | 8/2010 | Zou | | |

FOREIGN PATENT DOCUMENTS

| JP | 2012-187196 A | 10/2012 |
|---|---|---|
| JP | 2014-083234 A | 5/2014 |

\* cited by examiner

FIG.7A
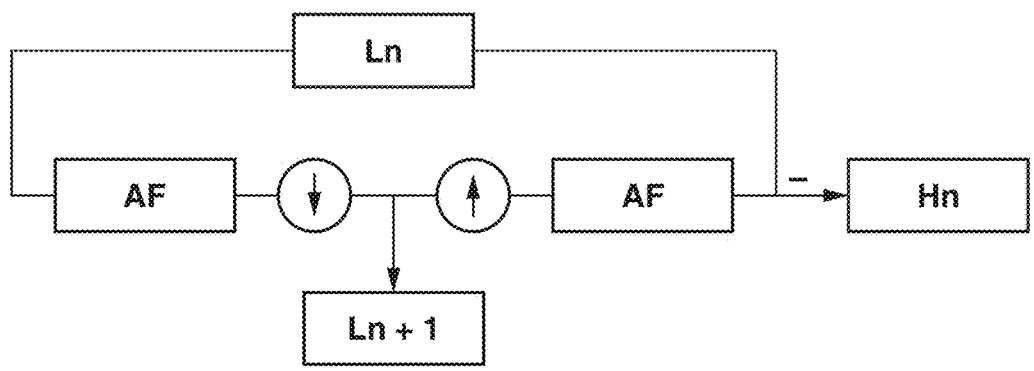
FIG.7B
| 0.0025 | 0.0125 | 0.02 | 0.0125 | 0.0025 |
|---|---|---|---|---|
| 0.0125 | 0.0625 | 0.1 | 0.0625 | 0.0125 |
| 0.02 | 0.1 | 0.16 | 0.1 | 0.02 |
| 0.0125 | 0.0625 | 0.1 | 0.0625 | 0.0125 |
| 0.0025 | 0.0125 | 0.02 | 0.0125 | 0.0025 |
FIG.7C
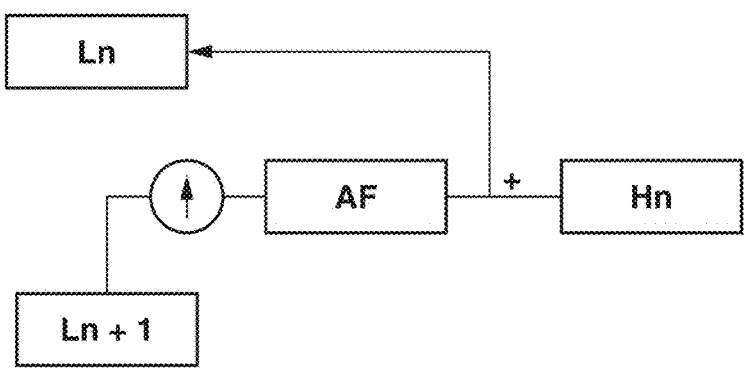

IMAGE PROCESSING APPARATUS, IMAGE PROCESSING SYSTEM, IMAGE PROCESSING METHOD, AND RECORDING MEDIUM

BACKGROUND

Field of the Invention

The present invention relates to an image processing apparatus for performing image processing on a radiation image, and a recording medium.

Description of the Related Art

A radiation image obtained by irradiating an object with a radiation includes not only a primary radiation component traveling straight from a radiation source but also a scattered radiation component which is a radiation scattered in the object. The scattered radiation component may possibly degrade the contrast of the radiation image. As a technique for reducing a scattered radiation component in an X-ray image, US2010/0208870 discusses a technique for obtaining a primary X-ray image in such a manner that the scattered radiation component is modeled using a formula obtained by performing a convolution of a formula expressed by a primary X-ray with two Gaussian functions.

FIG. 9A is a diagram illustrating an example in which measurement is performed by using a thoracic phantom and a scattered radiation component included in a radiation image is acquired on an experimental basis. Referring to FIG. 9A, the scattered radiation component includes what is called a skin line 903 at the boundary between a region (through-exposure region) 901 irradiated with an X-ray that passed through the periphery of an object without penetrating the object and an object region 902. This phenomenon occurs because, depending on the object's thickness, a radiation that entered the object scatters in a different mode and is not scattered in the through-exposure region 901 whereby an intensity distribution of the scattered X-ray becomes discontinuous.

SUMMARY

The inventors of the present invention carried out extensive studies, and as a result, found it possible to estimate the scattered radiation component by using the following method.

According to an aspect of the present invention, an image processing apparatus includes a receiver configured to receive a radiation image obtained by irradiating an object with a radiation, an image processor configured to estimate a scattered radiation component included in the radiation image acquired by the receiver, based on a first function corresponding to an intensity of a scattered radiation including a multiple-times scattered radiation which is a radiation scattered a plurality of times in the object and on a second function corresponding to an intensity of a single-time scattered radiation which is a radiation scattered once in the object, and a transmitter configured to transmit a corrected image obtained by reducing the scattered radiation component estimated by the image processor from the received radiation image.

Further features of the present invention will become apparent from the following description of exemplary embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

BRIEF DESCRIPTION OF THE DRAWINGS

FIGS. 7A, 7B, and 7C are diagrams illustrating frequency decomposition and image reconstruction based on Laplacian pyramid according to the another exemplary embodiment of the present invention.

DESCRIPTION OF THE EMBODIMENTS

Figure 1:
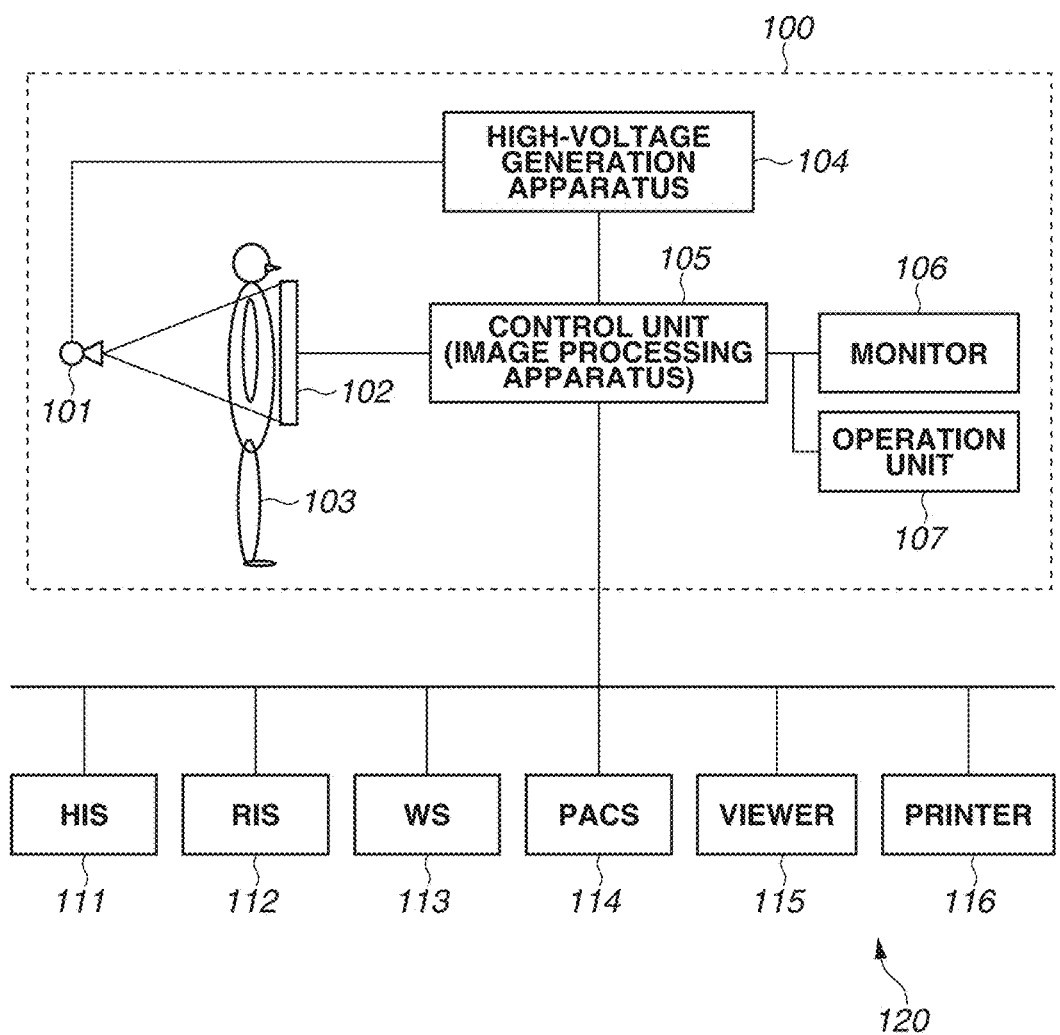
FIG. 1 is a diagram illustrating a configuration of an information system including an image processing apparatus according to an exemplary embodiment of the present invention.

An information system 120 including an image processing apparatus and a radiation imaging system 100 according to an exemplary embodiment of the present invention will be described below with reference to FIG. 1. The image processing apparatus according to the exemplary embodiment corresponds to a control unit 105 included in the radiation imaging system 100. The information system 120 includes, for example, a Hospital Information System (HIS) 111, a Radiography Information System (RIS) 112, a work station (WS) 113, an Picture Archiving and Communication System (PACS) 114, a viewer 115, and a printer 116. The HIS 111 is a system for totally managing patient information and medical information including, for example, inspections through radiation imaging. The RIS 112 is a system for managing radiation imaging orders. The WS 113 is an image processing terminal for performing image processing on a radiation image captured by the radiation imaging system 100. The WS 113 may be substituted for by one or a plurality of computers in which software having similar functions is installed. The PACS 114 is a database system for storing images obtained through radiation imaging in the information system 120 and images obtained by other medical image imaging apparatuses. The PACS 114 includes a storage unit (not illustrated) for storing medical images and associated information of the medical images, such as imaging conditions and patient information, and a controller (not illustrated) for managing information stored in the storage unit. The viewer 115 is an image diagnostic terminal for reading an image stored in the PACS 114 and displaying it for diagnosis. The printer 116 is, for example, a film printer for outputting an image stored in the PACS 114 to a film.

The radiation imaging system 100 according to the exemplary embodiment uses an X-ray as a radiation. The radiation imaging system 100 includes an X-ray source 101 as an example of a radiation generating apparatus, a Flat Panel Detector (FPD) 102, and a control unit 105. These apparatuses are connected via cables or a communication system. The control unit 105 associates a captured radiation image with information, such as the imaging conditions and patient information of when the radiation image is captured. For example, the control unit 105 associates information in conformance with the Digital Imaging and Communications in Medicine (DICOM) standard to generate a DICOM image file including radiation image data, patient information, and imaging conditions. The control unit 105 transmits the image file to the WS 113 and the PACS 114. An order of the imaging is transmitted, for example, from the RIS 112 to the control unit 105. The control unit 105 reads the imaging conditions from the storage unit (not illustrated) according to input information from the RIS 112.

The X-ray source 101 may be an X-ray tube or any other arbitrary radiation source suitable for acquisition of medical images and other images. When an operator presses an exposure switch, a high-voltage generation unit 104 applies a high-voltage pulse to the X-ray source 101, and the X-ray source 101 exposes to an X-ray a region in which an object 103 is disposed. The X-ray that penetrated the object 103 or passed the periphery of the object 103 enters the FPD 102 which is an X-ray detector. The FPD 102 controlled by the control unit 105 converts the incident X-ray into an electrical signal, and transmits the signal to the control unit 105 as a digital image. For example, in the FPD 102, a phosphor (not illustrated) converts the incident X-ray into visible light, a photodiode (not illustrated) detects the visible light, and an analog-to-digital (A/D) converter (not illustrated) converts the light into an electrical signal. Alternatively, the FPD 102 converts the X-ray into an electrical signal using amorphous selenium (not illustrated). The pixel value of a radiation image is acquired by an output from radiation detecting elements 102a constituting the FPD 102. The radiation detecting elements 102a are composed of, for example, phosphor (not illustrated) and photodiodes (not illustrated). In another example, the radiation detecting elements 102a are composed of amorphous selenium (not illustrated).

A digital image is subjected to image processing by the control unit 105 and the WS 113, and stored in the PACS 114. The units included in the information system 120 only need to be connected with each other via a bus or other communication system, and may be remotely installed.

Figure 2:
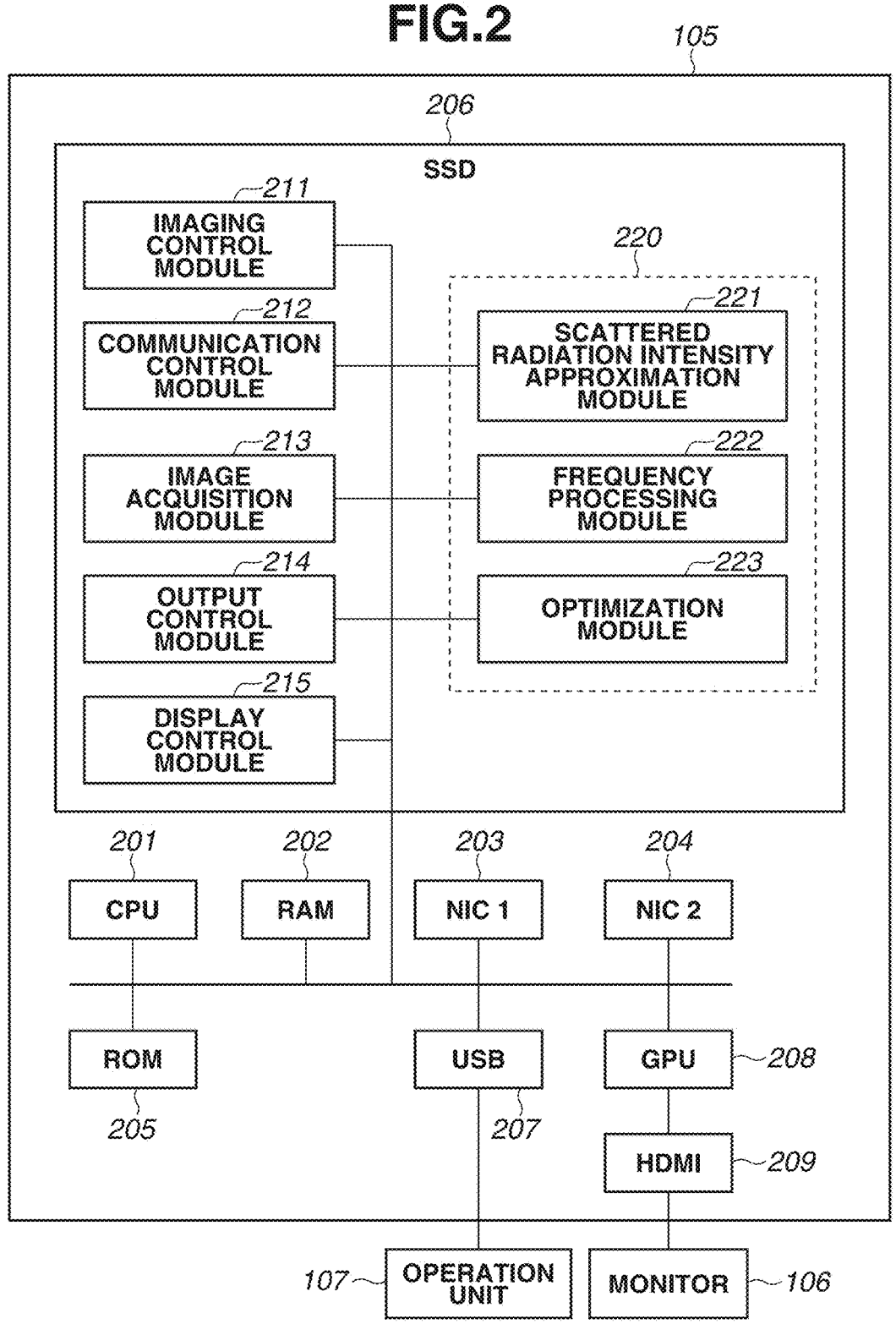
FIG. 2 is a diagram illustrating a configuration of the image processing apparatus according to the exemplary embodiment of the present invention.

The configuration of the image processing apparatus according to the exemplary embodiment of the present invention will be described below with reference to FIG. 2. The image processing apparatus according to the exemplary embodiment of the present invention is the control unit 105 connected with the radiation imaging system 100 included in the information system 120. The image processing apparatus includes one or a plurality of computers. The computer constituting the control unit 105 includes a central processing unit (CPU) 201 as a main control unit, a random access memory (RAM) 202 as a storage unit, a read only memory (ROM) 205, a solid state drive (SSD) 206, a graphics processing unit (GPU) 208 as a graphic control unit, network interface cards (NICs) 203 and 204 as communication units, a universal serial bus (USB) 207 as a connection unit, and a High Definition Multimedia Interface (HDMI) (registered trademark) 209 which are communicably connected with each other via an internal bus. The CPU 201 is a control circuit for totally controlling the control unit 105 and each unit connected thereto. The RAM 202 is a memory for storing programs for performing processing by the control unit 105 and each unit connected thereto, and storing various parameters to be used in image processing. The image processing (described below) is implemented when the CPU 201 sequentially executes instructions included in a program loaded into the RAM 202. For example, the first NIC 203 as a communications unit is connected to an access point of a facility for performing radiation imaging, and the second NIC 204 is connected to an access point for relaying communication in the information system 120. The SSD 206 stores the above-described programs, radiation images captured through imaging, associated information, and other various parameters. The USB 207 is connected to an operation unit 107. The GPU 208 is an image processing unit for performing image processing under control of the CPU 201. An image obtained as a result of image processing is output to a monitor 106 via the HDMI (registered trademark) 209 and displayed on the monitor 106. The monitor 106 and the operation unit 107 may be integrated into a touch panel monitor.

The programs stored in the SSD 206 include, for example, an imaging control module 211, a communication control module 212, an image acquisition module 213, an output control module 214, a display control module 215, and an estimation module 220.

The imaging control module 211 is a program for causing the CPU 201 to totally control the execution of radiation imaging. The imaging control module 211, for example, specifies imaging conditions in response to an operation input, and transmits a signal for requesting the status of the FPD 102.

The communication control module 212 controls communication by the first NIC 203 and the second NIC 204. The communication control module 212, for example, controls the first NIC 203 and the second NIC 204 to transmit a signal for causing the FPD 102 to shift to a state ready for imaging in response to the operation unit 107.

The image acquisition module 213 implemented by the CPU 201 controls a process of acquiring an image subjected to image processing according to the exemplary embodiment. For example, the image acquisition module 213 instructs the first NIC 203 to receive a radiation image captured by the FPD 102. When receiving a radiation image, the image acquisition module 213 instructs the first NIC 203 to receive a reduced image of the radiation image having a small data amount in advance and then receive data other than the reduced image of the radiation image to complete reception of the radiation image. The reduced image is obtained by using only output signals selectively read from some elements, for example, by reading even number columns out of a plurality of radiation detecting elements constituting the FPD 102 and providing the pixel values of the radiation image. Alternatively, some elements may be collectively read. Further, a read image may be divided into a plurality of small areas and a reduced image is generated by using representative values of the small areas. Alternatively, the first NIC 203 receives a radiation image stored in the PACS 114 and a storage unit on a network. Alternatively, the first NIC 203 reads out a radiation image stored in the SSD 206 and other storage unit of the image processing apparatus 105. Further, before an image is subjected to the image processing according to the exemplary embodiment of the present invention, the CPU 201 may perform control in such a manner that well-known image processing is performed on the image.

The estimation module 220 implemented by the CPU 201 estimates the primary radiation component or the scattered radiation component of the radiation image based on an assumption that the radiation image is represented by the sum of the primary radiation component and the scattered radiation component and an assumption that the scattered radiation component can be obtained from the primary radiation component through a scattered radiation model. The estimation module 220 includes, for example, a scattered radiation intensity approximation module 221, a frequency processing module 222, and an optimization module 223. These modules are implemented by the CPU 201. Thus, the CPU 201 controls the GPU 208 to perform scattered radiation component estimation processing.

The scattered radiation intensity approximation module 221 implemented by the CPU 201 obtains the intensity of the scattered radiation component by input of a primary radiation component P. For example, for the first function, the scattered radiation intensity approximation module 221 inputs an n-th order approximate solution $P_n$ of the primary radiation component to obtain first output data. Further, for the second function, the scattered radiation intensity approximation module 221 inputs an n-th order approximate solution $P_n$ of the primary radiation component to obtain second output data.

The frequency processing module 222 implemented by the CPU 201 obtains a specific frequency component of function output. For example, the frequency processing module 222 convolutes the Gaussian function $G_1$ with the first output data to obtain a specific frequency component of the first output data. The frequency processing module 222 further convolutes the Gaussian function $G_2$ with the second output data to obtain a specific frequency component of the second output data. Then, the frequency processing module 222 weights and combines these pieces of output data with a predetermined ratio to obtain an n-th order approximate solution $S_n$ of the scattered radiation component.

The optimization module 223 implemented by the CPU 201 obtains $P_{n+1}$ based on $P_n$ and $S_n$ using a recurrence formula based on the successive approximation method. The obtained value is input again to the scattered radiation intensity approximation module 221. The optimization module 223 performs a convergence test and repeats the processing in a similar order until the value is determined to have converged. When the optimization module 223 determines that the value have converged, approximate solutions, for example, $P_n$ and $S_n$ are assumed to be results of estimation of the primary radiation component and the scattered radiation component of the radiation image, respectively. The processing will be described in detail below with reference to FIG. 3.

The output control module 214 implemented by the CPU 201 controls output of a corrected image obtained by reducing the scattered radiation component through the image processing according to the exemplary embodiment of the present invention. For example, the output control module 214 outputs the corrected image to the monitor 106 to display it on the monitor 106. For example, the output control module 214 outputs the corrected image to the PACS 114 and the printer 116 via the second NIC 204. Thus, the corrected image is stored in the PACS 114 and output to a film by the printer 116. The output module 214 may output the corrected image to a storage unit (not illustrated) inside or outside the control unit 105 to store it. Further, it is desirable to associate various information with the corrected image in conformance with the DICOM standard and then output the corrected image. A modality refers to an image generation apparatus for capturing an image of a patient and generating a medical image. In the information system 120 according to the exemplary embodiment of the present invention, for example, the radiation imaging system 100 including the X-ray source 101 and the FPD 102 corresponds to a modality. In this case, DX indicating Digital Radiography is associated with an image as a Modality tag (0008, 0060). In case of moving image capturing, RF indicating Radio Fluoroscopy is associated with an image. Further, when the data is stored in the PACS 114, as a Service Object Pair Class Unique Identifier (SOP Class UID) (0008, 0016) tag for specifying a Pair of Service and Object, "1.2.840.10008.5.1.4.1.1.1.1" indicating a combination of Digital X-ray Image of Object and Storage of Service is associated with the image.

The display control module 215 controls the contents displayed on the monitor 106. For example, the display control module 215 performs control for displaying of patient information, imaging condition information, and information indicating the status of the FPD 102 on the monitor 106. These pieces of information are displayed on the monitor 106 together with the above-described corrected image.

In another exemplary embodiment, the display control module 215 may perform display control for displaying of the corrected image on the monitor 106, which is performed by the output control module 214. In this case, the display control module 215 displays on a display screen the captured radiation image and the corrected image.

The control unit 105 is the operating entity for performing image processing according to the exemplary embodiment of the present invention. Hereinafter, the control unit 105 may be referred to as an image processing apparatus 105 from the viewpoint of describing the image processing according to the exemplary embodiment of the present invention.

A part or whole of components of the control unit 105 is not fixed to the control unit 105, and may be implemented as an image processing system included in the information system 120. For example, the image processing apparatus including the image acquisition module 213, the output control module 214, and the estimation module 220 and executing an image processing program may be provided separately from the control unit 105 for executing the imaging control module 211. Further, for example, the WS 113 may include a part or whole of the above-described modules. The PACS 114 may include a part or whole of the above-described modules. The FPD 102 may include, for example, a field-programmable gate array (FPGA) having the estimation module 220. The components included in the control unit 105 may be included in different apparatuses in a duplicated way, and an apparatus for performing processing may be selected according to an operator's instruction. Further, the control unit 105 may include a workstation, a server, and a storage device connected via a network, and may communicate with these apparatuses as required to perform the image processing according to the exemplary embodiment of the present invention.

Figure 3:
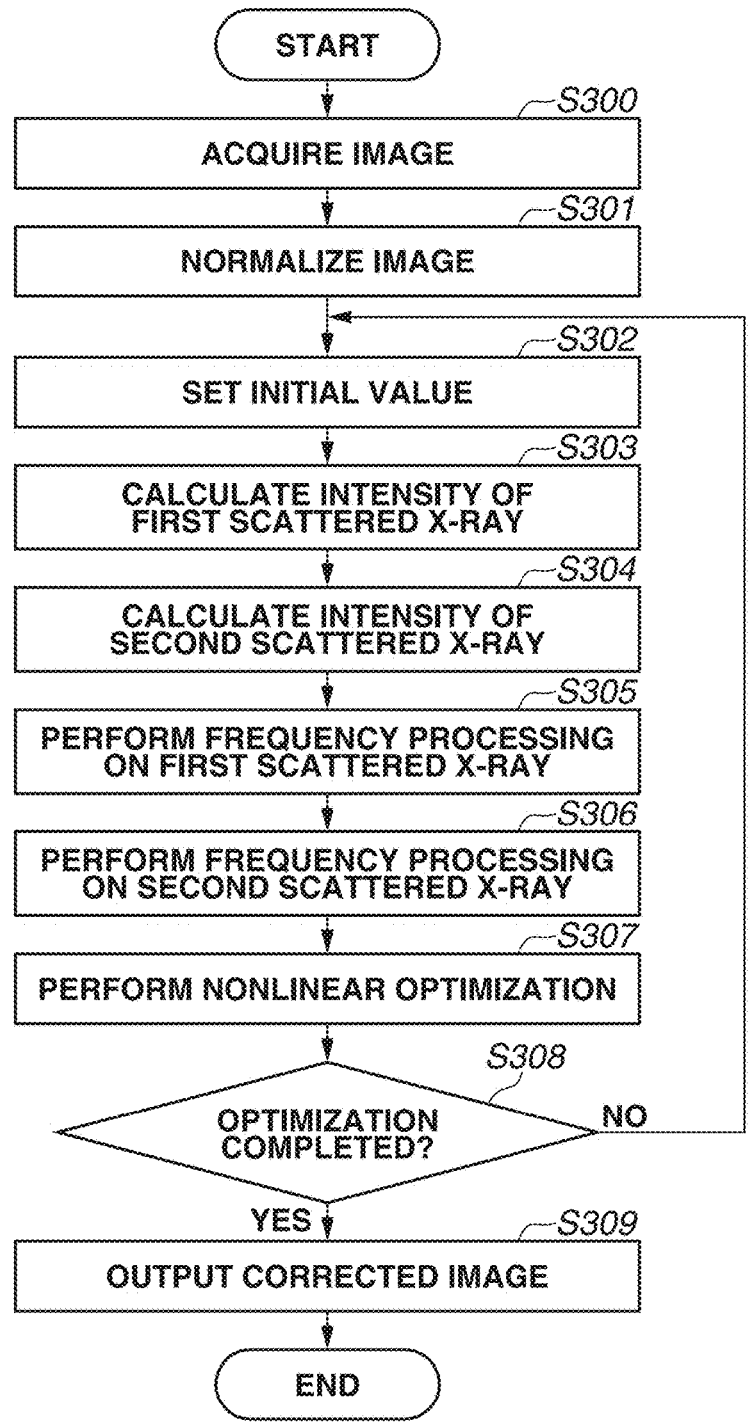
FIG. 3 is a flowchart illustrating processing according to the exemplary embodiment of the present invention.

The image processing performed by the control unit 105 will be described below with reference to FIG. 3. In the following processing, unless otherwise noted, the CPU 201 or the GPU 208 is the operating entity. The estimation module 220 implemented by the CPU 201 performs the following processing for estimating the scattered radiation component.

The image obtained by radiation imaging is composed of the primary X-ray image based on the primary X-ray that has been linearly reached each element of the FPD 102 from the X-ray source 101, and the scattered X-ray image based on the scattered X-ray (an X-ray scattered in the object 103), and the scattered X-ray image is superimposed on the primary X-ray image.

The relation of these images is represented by $$M'(x,y)=P'(x,y)+S'(x,y) \quad (1),$$

where M'(x,y) indicates an image (input image) obtained by radiation imaging, P'(x,y) indicates the primary X-ray component included in the input image, and S'(x,y) indicates the scattered X-ray component in the input image, and the coordinates (x,y) indicate the pixel position of the image or the element position of the FPD 102 providing the pixel value of the pixel position.

The scattered X-ray results from the X-ray scattering in the process where the X-ray emitted from the X-ray source 101 penetrates the object 103, and the component which is not scattered is the primary X-ray component. Therefore, S'(x,y) has a correlation with P'(x,y). However, this correlation is nonlinear as represented by formulas (described below). Therefore, the image processing apparatus 105 optimizes S'(x,y) and P'(x,y) through repetitive processing, and uses the maximum likelihood estimation. There are other various nonlinear optimization techniques, such as the least-square method, the Newton's method, and the convex analysis, and any method may be used.

In step S300, the image acquisition module 213 implemented by the CPU 201 acquires a radiation image captured by irradiating the object 103 with a radiation. The radiation image is an input image subjected to the scattered radiation component estimation processing. By acquiring a reduced image with a small data amount as the input image, and using the reduced image for the estimation processing, it is possible to perform data transmission from the FPD 102 and subsequent image processing at higher speed. Since the scattered radiation component mainly includes a low-frequency component, even the estimation processing is performed based on the reduced image, there is a small influence on the accuracy of estimating the scattered radiation component.

In step S301, the scattered radiation intensity approximation module 221 implemented by the CPU 201 normalizes the input image. For example, the sum total value of the primary X-ray dose and the scattered X-ray dose having reached the FPD 102 are normalized with the incident dose to the object 103. The incident dose may be defined as a radiation dose detected by the FPD 102 when the object 103 is assumed to be absent. The incident dose may be estimated from imaging conditions, such as the X-ray tube voltage, the X-ray tube current, the irradiation duration, and the imaging target portion, and may be obtained from the pixel value of a region (through-exposure region) reached by an X-ray that has not penetrated the object 103. When normalization is performed with an incident dose Q, M(x,y), P(x,y), and S(x,y) are represented by the following Formulas (2), (3), and (4), respectively:

$$\frac{M'(x, y)}{Q} = M(x, y), \quad (2)$$

$$\frac{P'(x, y)}{Q} = P(x, y), \text{ and} \quad (3)$$

$$\frac{S'(x, y)}{Q} = S(x, y). \quad (4)$$

Hereinafter, M(x,y), P(x,y), and S(x,y) are treated as normalized values.

In step S302, the scattered radiation intensity approximation module 221 implemented by the CPU 201 sets an initial value $P^0(x,y)$ of P(x,y) in the maximum likelihood estimation. The initial value $P^0(x,y)$ should be a positive value. M(x,y) is used as the initial value in the present exemplary embodiment since the primary X-ray component P(x,y) is assumed to be close to the input image M(x,y).

Figure 4:
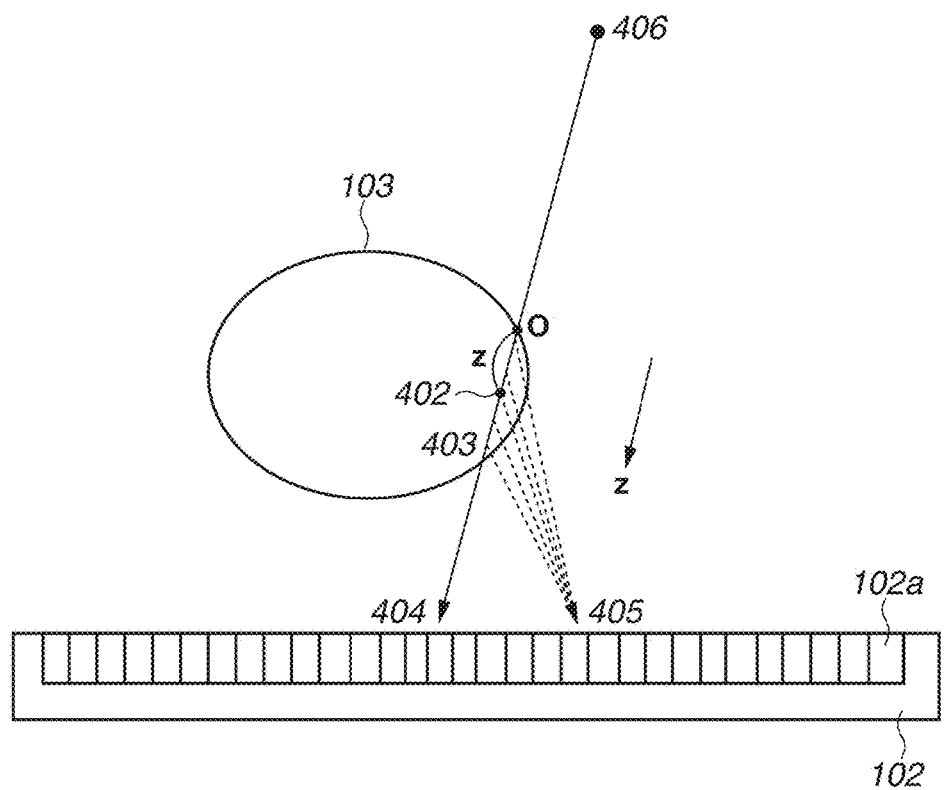
FIG. 4 is a diagram illustrating an example of a scattered X-ray approximated by using a first function according to the exemplary embodiment of the present invention.

In step S303, the scattered radiation intensity approximation module 221 implemented by the CPU 201 calculates the first scattered X-ray intensity as the first output data obtained, for example, by substituting the input image M into the first function. The first function refers to a function (approximation formula) that approximated the scattered radiation intensity by the scattered X-ray which results from the scattering of the X-ray and is assumed not to be attenuated after the scattering. The first output data refers to output data of the first function. FIG. 4 is a diagram illustrating an example of a scattered X-ray approximated by the first function. It is assumed that the scattered X-ray resulting from the X-ray scattering on a path L 403, which is from a focus 406 of the X-ray source 101 and passes through a certain position 402 in the object 103, reaches a certain element position 404 (x,y) among the radiation detecting elements 102a, without being attenuated after scattering. The z axis is set on the path L 403 from the focus 406 to the element position 404, and the positive direction of the z axis is the traveling direction of the primary X-ray. The origin is the position where the X-ray enters the object 103. The attenuation coefficient is a value p which is constant in the object 103. In this case, the scattered X-ray resulting from the X-ray scattering at a position z 402 on the path L 403 in the object 103 is proportional to $$\mu\exp(-\mu z)dz \quad (5).$$

Further, a normalized primary X-ray P satisfies $$P=\exp(-\mu L) \quad (6).$$

Therefore, the total intensity of the first scattered X-ray resulting from the X-ray scattering on the path L 403 and reaches the element position 404 (x,y) without being attenuated after scattering is represented by $$\int_0^L \mu\exp(-\mu z)dz = 1-\exp(-\mu L) = 1-P \quad (7),$$

which is a function of the primary X-ray component P(x,y). More specifically, for example, 1−P is the first function.

It may be considered that the first function approximates the radiation has entered the object 103 and scattered at the position 402 and reached an element position 405 of the through-exposure region almost without being attenuated after scattering, to the radiation which has traveled the linear path from the X-ray source 101 to the element position 404.

Figure 5:
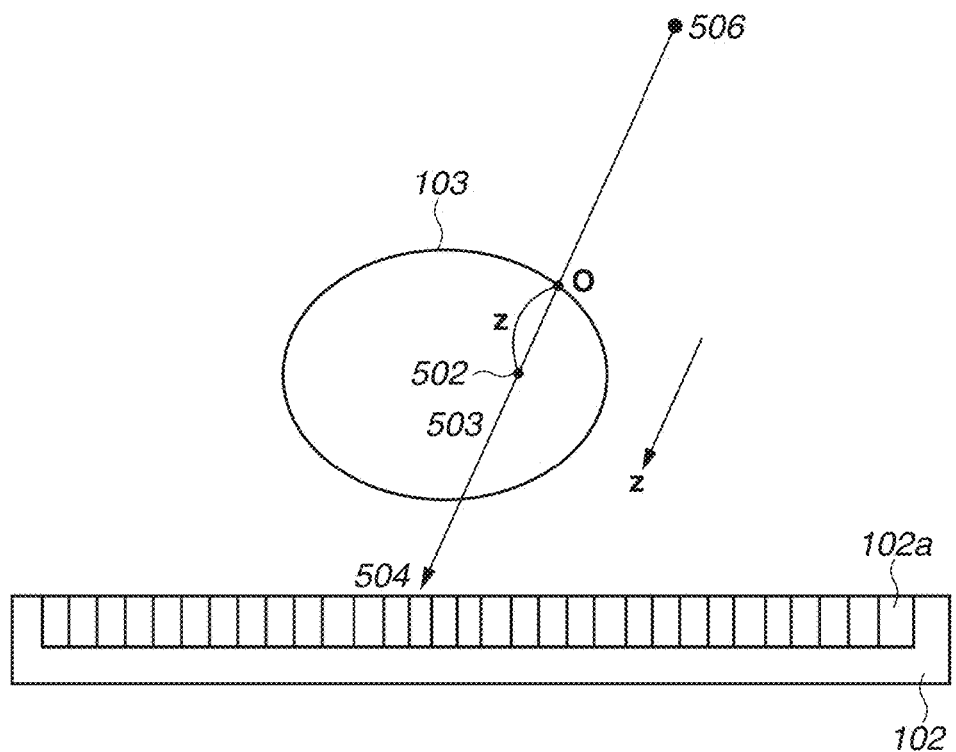
FIG. 5 is a diagram illustrating an example of a scattered X-ray approximated by using a second function according to the exemplary embodiment of the present invention.

In the image processing apparatus 105, it is desirable to estimate the scattered radiation image based on a plurality of functions different from the first function. In step S304, the scattered radiation intensity approximation module 221 implemented by the CPU 201 calculates the second scattered X-ray intensity as the second output data obtained, for example, by substituting the input image M into the second function. The second function refers to a function (approximation formula) that approximated the scattered radiation intensity by the scattered X-ray which results from the scattering of the X-ray and is assumed to be further attenuated in the object 103 after the scattering. The second output data refers to output data of the second function. FIG. 5 is a diagram illustrating an example of a scattered X-ray approximated by the second function. This example approximates the scattered X-ray which mainly penetrated the inside of the object 103. It is assumed that a scattered X-ray resulting from the X-ray scattering on a path L 503, which is from a focus 506 of the X-ray source 101 and passes through a certain element position 504($x,y$) among the radiation detecting elements 102a, passes through the path L 503 while being attenuated and then enters the FPD 102. In this case, the z axis is set on the path L 503 from the focus 506 to the element position 504, and the positive direction of the z axis is the traveling direction of the primary radiation. The origin is the position where the X-ray enters the object 103. The attenuation coefficient is μ. In this case, the scattered X-ray resulting from the X-ray scattering at a position z 502 on the path L 503 in the object 103 is proportional to Formula (2). Further, assuming that the scattered X-ray penetrates the object 103 over a distance L-z while being attenuated, the total intensity of the second scattered X-ray resulting from the X-ray scattering on the path L 503 is represented by $$\int_0^L \mu \exp(-\mu z)\exp(-\mu(L-z))dz = \mu L\exp(=\mu L) = -P \ln P \quad (8),$$

which is a function of the primary X-ray component P(x,y). More specifically, for example, –P ln P is the second function.

Taking into consideration the fact that the scattered X-ray is scattered in a wide angle in the object 103, it is desirable to combine specific frequency components of output data of respective functions and estimate the scattered radiation component. In step S305, the frequency processing module 222 implemented by the CPU 201 performs frequency processing to decompose the output data obtained in the processing in up to step S304 into a plurality of frequency components. First of all, since the scattered X-ray component mainly includes a low-frequency component, convolution of the Gaussian function $G_1$ is performed. The low-frequency component of the first output data is represented by $$(1-P(x,y))*G_1 \quad (9), \text{ and}$$

$$G_1 = \exp(-B_1(x^2+y^2)) \quad (10).$$

Further, when the discontinuity of the scattered X-ray is taken into consideration, it is desirable to consider a non-low-frequency component. The non-low-frequency component of a scattered radiation image by a first scattered X-ray model is represented by $$(1-P(x,y))=F^{-1}(1-F(G_1)) \quad (11)$$

where F denotes Fourier transform and $F^{-1}$ denotes inverse Fourier transform.

The frequency processing module 222 implemented by the CPU 201 weights and combines by using parameters $A_1$ and $C_1$ a plurality of frequency components obtained in the above-described processing. Thus, a frequency component $S_1$ for the first output data is obtained.

According to the result of the above-described processing, $S_1$ is represented by $$S_1=-A_1(1-P(x,y))*G_1-C_1(1-P(x,y))*F^{-1}(1-F(G_1)) \quad (12),$$

where $A_1$ denotes the weight for the low-frequency component of the first scattered X-ray, $B_1$ denotes the spread of the first scattered X-ray, and $C_1$ denotes the weight for the non-low-frequency component of the first scattered X-ray.

In step S306, the CPU 201 obtains a specific frequency component of the second output data through the process similar to step S305. After convolution of the Gaussian function $G_2$, the low-frequency component is represented by $$-P(x,y)\ln P(x,y)*G_2 \quad (13), \text{ and}$$

$$G_2=\exp(-B_2(x^2+y^2)) \quad (14).$$

The non-low-frequency component is represented by $$-P(x,y)\ln P(x,y)*F^{-1}(1-F(G_2)) \quad (15).$$

The frequency processing module 222 implemented by the CPU 201 weights and combines by using parameters $A_2$ and $C_2$ a plurality of frequency components obtained in the above-described processing. Thus, a frequency component $S_2$ for the second output data is obtained.

According to the result of the above-described processing, $S_2$ is represented by $$S_2=-A_2(-P(x,y)\ln P(x,y))*G_2-C_2(-P(x,y)\ln P(x,y))\\*F^{-1}(1-F(G_2)) \quad (16),$$

where $A_2$ denotes the weight for the low-frequency component of the second scattered X-ray, $B_2$ denotes the spread of the second scattered X-ray, and $C_2$ denotes the weight for the non-low-frequency component of the second scattered X-ray.

The Gaussian functions $G_1$ and $G_2$ may be the same. It is desirable to decompose the first and the second output data into a plurality of different frequency bands, and then weight and combine the relevant frequency components.

Two different components respectively represented by Formulas (9) and (11) are described above as examples of frequency components of the first output data. Two different components respectively represented by Formulas (13) and (15) are described as examples of frequency components of the second output data. At least one of the two different frequency components of the first output data and at least one of the two different frequency components of the second output data may be weighted and combined into the scattered radiation component.

The above-described processing enables obtaining the scattered radiation component based on the frequency component $S_1$ of the first output data and the frequency component $S_2$ of the second output data. More specifically, the scattered radiation model in the image processing apparatus 105 is a scattered radiation model for obtaining the scattered radiation component based on a specific frequency component of the output of the first function and a specific frequency component of the output of the second function which is different from the first function.

A plurality of combinations of parameters $A_1$, $B_1$, $C_1$, $A_2$, $B_2$, and $C_2$ may be stored in the RAM 202, and these may be automatically set or suitably set by the operator. The image processing apparatus 105 may include a setting module for setting combination weights according to imaging conditions of the radiation image, such as the X-ray tube current and the X-ray tube voltage of the X-ray tube, the X-ray irradiation duration, and the imaging target portion. For example, the setting module acquires information of the above-described imaging conditions in response to an operation input on the operation unit 107, and then obtains the parameter set ($A_1$, $B_1$, $C_1$, $A_2$, $B_2$, and $C_2$) corresponding to the imaging conditions. Table information indicating the correspondence relation between the imaging conditions and the parameter set is pre-stored in the SSD 206. The CPU 201 refers to the table information to set the parameter set. The table information is defined, for example, for each imaging condition on an experimental basis.

As described above, since the scattered X-ray component mainly includes a low-frequency component, it is desirable that the parameters $A_1$ and $A_2$ indicating the weight for the low-frequency component have larger values than the parameters $C_1$ and $C_2$ indicating the weight for the non-low-frequency component.

The frequency processing module 222 may generate the low-frequency component and the non-low-frequency component in real space or by using Fourier transform. Further, the filter which is used for the frequency processing is not limited to the Gaussian functions. For example, the use of a weighted average filter enables representing the spread centering on the periphery of a target pixel, and the use of a moving average filter enables representing the spread from a target pixel to a distant pixel.

Although steps are described in order of steps S303, S304, S305, and S306, processing may be performed in order of steps S303, S305, S304, and S306. Processing in steps S303 and S305 and processing in steps S304 and S306 may be performed in parallel.

In step S307, the optimization module 223 implemented by the CPU 201 combines the frequency component of the first output and the frequency component of the second output calculated in up to step S306 to obtain the scattered radiation component, and performs the maximum likelihood estimation on the primary X-ray component. In the maximum likelihood estimation, for example, the optimization module 223 divides the input image $M(x,y)$ by the sum of the primary X-ray component $P^n(x,y)$, the frequency component $S_1^n(x,y)$ of the first output data, and the frequency component $S_2^n(x,y)$ of the second output data obtained in the preceding stage of repetition, and then multiplies the result by the primary X-ray component $P^n(x,y)$, which is represented by $$P^{n+1}(x, y) = \frac{M(x, y)}{P^n(x, y) + S_1^n(x, y) + S_2^n(x, y)} P^n(x, y), \quad (17)$$

where the superscript n indicates that the value obtained in the n-th repetition.

It is known that in the maximum likelihood estimation represented by Formula (17), each time the processing is repeated, the following Formula (18) converges to 1:

$$\frac{M(x, y)}{P^n(x, y) + S_1^n(x, y) + S_2^n(x, y)}. \quad (18)$$

The optimization module 223 successively obtains the primary X-ray component $P(x,y)$, the frequency component $S_1(x,y)$ of the first output data, and the frequency component $S_2(x,y)$ of the second output data so that the relation represented by Formula (1) is satisfied.

In step S308, the optimization module 223 implemented by the CPU 201 determines whether the processing is to be repetitively continued. The optimization module 223 performs the determination by determining whether Formula (18) has been sufficiently closed to 1 or whether the relation represented by Formula (1) is fully satisfied based on a square residual error. Alternatively, the optimization module 223 performs the determination by determining whether the processing is repeated for a fixed number of times.

In a case where the optimization module 223 determines that the processing is to be repetitively continued (NO in step S308), the processing returns to step S302. Then, in step S302, the optimization module 223 repeats the processing by using the calculated $P^{n+1}(x,y)$ as an initial value. In a case where the optimization module 223 determines the processing is not to be repetitively continued (YES in step S308), the processing proceeds to step S309. Then, in step S309, the optimization module 223 uses $P^{n+1}(x,y)$ as a corrected image in which the scattered X-ray component is reduced. Alternatively, the optimization module 223 may multiply the sum of the calculated $S_1^{n+1}(x,y)$ and $S_2^{n+1}(x,y)$ by a parameter, and subtract the result from the input image. More specifically, the effect of reducing the scattered radiation image may be made adjustable.

As described above, the image processing apparatus 105 outputs the scattered radiation component $S_1(x,y)+S_2(x,y)$ which combines specific frequency components of the first and the second output data, respectively. Further, the image processing apparatus 105 derives the scattered radiation component included in the radiation image by using the successive approximation method on an assumption that the sum of the scattered radiation component and the primary X-ray component coincides with the input image.

In step S309, the output control module 214 implemented by the CPU 201 outputs the corrected image obtained in the above-described processing. In the process, the corrected image is stored in the PACS 114 and displayed on the monitor 106. The estimated scattered X-ray image $S_1^{n+1}(x,y)+S_2^{n+1}(x,y)$ may be stored in the PACS 114 as image data or an image file different from the relevant corrected image.

From another viewpoint, each of the first and the second functions approximates the total intensity of the scattered radiation resulting from the X-ray scattering on a path from the focus 406 to each radiation detecting element 102a providing the pixel value of the radiation image, for each path by using a plurality of scattered radiation models attenuated at different distances on each path. In the above-described processing, the estimation module 220 estimates a scattered radiation image by uniformly performing the approximation processing on the pixel value corresponding to the output from each of the radiation detecting elements 102a. This eliminates the need of changing a model for each pixel value included in the radiation image whereby it becomes possible to reduce time and resources required for the scattered radiation component estimation processing.

Further, the distance at which radiation is attenuated after scattering can be adjusted by parameters. For example, assuming that radiation is attenuated at a distance x and is not attenuated at other distances in the object 103 after scattering, the total intensity of the scattered radiation is represented by $$\int_0^L \mu\exp(-\mu z)\exp(-\mu x)dz = \exp(-\mu x)(1-\exp(-\mu L)) = X(1-P) \quad (19),$$

where x satisfies a condition "$0<x<(L-z)$."

Assuming that radiation is attenuated in the object 103 after scattering but not attenuated at a distance y, the total intensity of the scattered radiation is represented by $$\int_0^L \mu\exp(-\mu z)\exp(-\mu(L-z))\exp(-\mu y)dx = \exp(-\mu y)\mu L\exp(-\mu L) = Y(-P \ln P) \quad (20),$$

where y satisfies a condition "$0<y<(L-z)$."

X and Y may be included in the parameters $A_1$, $B_1$, $C_1$, $A_2$, $B_2$, and $C_2$. Therefore, the present invention is not limited to the above-described two models, and may include models approximated at various attenuation distances by suitably selecting parameters.

The parameters $A_1$, $B_1$, $C_1$, $A_2$, $B_2$, and $C_2$ may be multiplied by any term within an equivalent transformation range. More specifically, the first and the second functions are not limited to the above-described concept of the approximation of the scattered radiation intensity, and the present invention includes the multiplication of other term by each parameter.

Further, the first function in the image processing apparatus 105 is not limited to 1−P. The function 1−P has the following characteristics: (1-1) The function outputs minimum value (0) when P is maximum value (1) in a normalized radiation image, (1-2) The function outputs positive value (1) when P is minimum value (0), (1-3) The function is converged to a positive value when P comes close to the minimum value, (1-4) The function monotonically decreases within the range of P from 0 to 1, and (1-5) The derived function outputs a negative value when P is 0, where P is a variable related to a intensity of a primary radiation which is a radiation having traveled straight from a radiation generating apparatus to a radiation detecting element for providing a pixel value of the received radiation image. More specifically, the first function may be a function which satisfies a part or whole of the characteristics (1-1) to (1-5) and indicates the correspondence relation between the value of the primary radiation component and the value of the scattered radiation component. For example, the following Formula (21) is given:

$$-0.05P^2 - 0.9P + 0.95 \qquad (21).$$

The second function in the image processing apparatus 105 is not limited to −P ln P. The function −P ln P has the following characteristics: (2-1) The function outputs minimum value (0) when P is maximum value (1) in a normalized radiation image, (2-2) The function outputs minimum value (0) when P is minimum value (0), (2-3) The function outputs a positive value when P is neither 0 nor 1, (2-4) The function outputs a local maximum value within the range of P from 0 to 1, and (2-5) The derived function outputs a positive value when P is 0, where P is a variable related to a intensity of a primary radiation which is a radiation having traveled straight from a radiation generating apparatus to a radiation detecting element for providing a pixel value of the received radiation image. More specifically, the second function may be a function which satisfies a part or whole of the characteristics (2-1) to (2-5) and indicates the correspondence relation between the value of the primary radiation component and the value of the scattered radiation component. For example, the following Formula (22) is given:

$$0.8P^3 - 2.61P^2 + 1.74P \qquad (22).$$

The above-described first or second function may not be represented by the above-described formula, and may be represented, for example, by a lookup table indicating the output values for the values of the primary X-ray component P.

In a case where the primary X-ray largely decreases and a large amount of scattered X-ray results from the scattering of the X-ray, for example, in a case where the object 103 is thick, performing estimation based on the first function enables estimating the scattered radiation component with sufficient accuracy. For example, the primary X-ray hardly passes through thick portions of the object 103. More specifically, when P nearly equals 0, performing estimation based on the second function also estimates the scattered X-ray intensity as a value close to 0. However, performing estimation based on the first function estimates the scattered X-ray intensity as a value close to 1, and hence the scattered X-ray that is actually resulting from the scattering of the X-ray is not estimated smaller, so that estimation can be performed with sufficient accuracy. Further, in view of the fact that the scattered X-ray largely spreads, by decomposing the data into a plurality of frequency components and combining the frequency components by using parameters in consideration of the spreading condition for each component, it is possible to estimate with sufficient accuracy the scattered X-ray spreading over regions where the object 103 is absent and thin portions of the object 103. As a result, the scattered radiation image can be estimated more correctly in portions where the object 103 is absent and in a lung field region 904 and the skin line 903 illustrated in FIG. 9A.

In another viewpoint, the second function −P ln P may be considered as a function based on an assumption that the single-time scattered X-ray results from the attenuation of the incident X-ray and there are no multiple-times scattered X-ray that results from the process where the single-time scattered X-ray is attenuated in the object 103. According to this viewpoint, the first function 1−P may be considered as a function based on an assumption that the single-time scattered X-ray results from the attenuation of the incident X-ray, and the single-time scattered X-ray is not absorbed by the object 103 and a multiple-times scattered X-ray results from the X-ray scattering in the process where the single-time scattered X-ray passes through the object 103 and is attenuated therein. The scattered X-ray results from the X-ray scattering in the object 103, in fact, may cause a multiple-times scattered X-ray. That is, weighting and combining the output data of the first function 1−P to the output data of the second function −P ln P refer to weighting and combining the multiple-times scattered X-ray which may result from the X-ray incident on the object 103 and the ratio of the single-time scattered X-ray. This enables suitably representing the attenuation condition of the scattered X-ray resulting from the X-ray scattering in the object 103, improving the quantities characteristics of the estimated scattered radiation component. More specifically, the scattered radiation component can be more correctly estimated. By obtaining specific frequency components of output data of the two different functions and combining the relevant frequency components, it is possible to take into consideration the difference in spread between scattered X-rays having different attenuation conditions, so that the accuracy is improved in estimating the scattered radiation component.

In addition to the first and the second functions, a function from among the above-described various functions may also be used as a third function. In this case, the scattered radiation component is estimated by using output data obtained by substituting the input image or P″(x,y) (an approximate solution calculated by Formula (17)) into the first, the second, and the third functions. Although the third function may be the same as the first or the second function, it is desirable to combine different frequency components of respective output data. For example, a specific frequency component may be obtained by using the Gaussian function $G_3$ for the third output data, and the frequency component of the first output data and the frequency component of the second output data may be weighted and combined, as represented by $$[-0.05\{P(x,y)\}^2 - 0.9P(x,y) + 0.95] + G_3 \qquad (23).$$

A scattered radiation model to be applied to the radiation image only needs to express that the scattered radiation is attenuated at different distances in the object 103 and that there are various ways resulting in a multiple-times scattered radiation from another viewpoint. More specifically, even in case of a single function, it is necessary to weight and combine at least two frequency components which are obtained by decomposing the data into a plurality of frequency components. Using different parameters enables expressing different behaviors of the scattered radiation. Taking into consideration spread of at least two components (the lower frequency component and the higher frequency component) enables estimating changes in the scattered radiation distribution. For example, the components respectively represented by Formulas (9) and (11) may be weighted and combined.

The phenomenon in which the X-ray is attenuated in the object 103 is a phenomenon in which the X-ray is scattered and absorbed. As a result, the X-ray reaching the FPD 102 provides a lower intensity than the incident X-ray to the object 103. The scattered X-ray that results from the X-ray scattering in the object 103 and is attenuated according to the penetration distance after the scattering refers to the scattered X-ray based on an assumption of a case where only the single-time scattered X-ray is detected by the FPD 102. In this case, the scattered X-ray resulting from the X-ray scattering once further results in a multiple-times scattered X-ray or is absorbed in the process of penetration after scattering, and the multiple-times scattered radiation does not reach the FPD 102. Such a scattered X-ray is considered to be predominant in thick portions of the object 103. The scattered X-ray that results from the X-ray scattering in the object 103 and is not attenuated after scattering refers to a scattered X-ray based on an assumption of a case where the radiation is not absorbed in the object 103 and a multiple-times scattered X-ray resulting from the X-ray scattering is entirely detected by the FPD 102. The scattered X-ray reaching thin portions of the object 103 and the through-exposure region as the result of scattering and spread is considered to include not only the single-time scattered X-ray but also the multiple-times scattered X-ray. Therefore, performing estimation based on functions, which is based on assumptions of the above-described two cases, enables more correctly representing a mode in which radiations are attenuated or scattered in the object 103.

Although scattered radiation models have specifically been described above from various viewpoints, the above-described modifications of functions can also be used in a case where the scattered radiation models are grasped from any viewpoint, and are included in the present invention.

As described above, performing estimation based on the first function and the second function different from the first function enables estimating the scattered radiation image with sufficient accuracy. Further, by weighting and combining not only the lower frequency component but also at least two frequency components obtained by decomposing the data into a plurality of frequency components, it is possible to estimate the scattered radiation component including the boundary where the scattered radiation distribution changes.

Another exemplary embodiment of the present invention will be described below. Similar to the above-described exemplary embodiment, the another exemplary embodiment estimates the scattered radiation component included in the radiation image by applying to the radiation image a scattered radiation model for obtaining the scattered radiation component based on a specific frequency component of the output of the first function and a specific frequency component of the output of the second function different from the first function. In this case, the first output data and the second output data are decomposed into at least three frequency bands and then frequency components are obtained.

Figure 6:
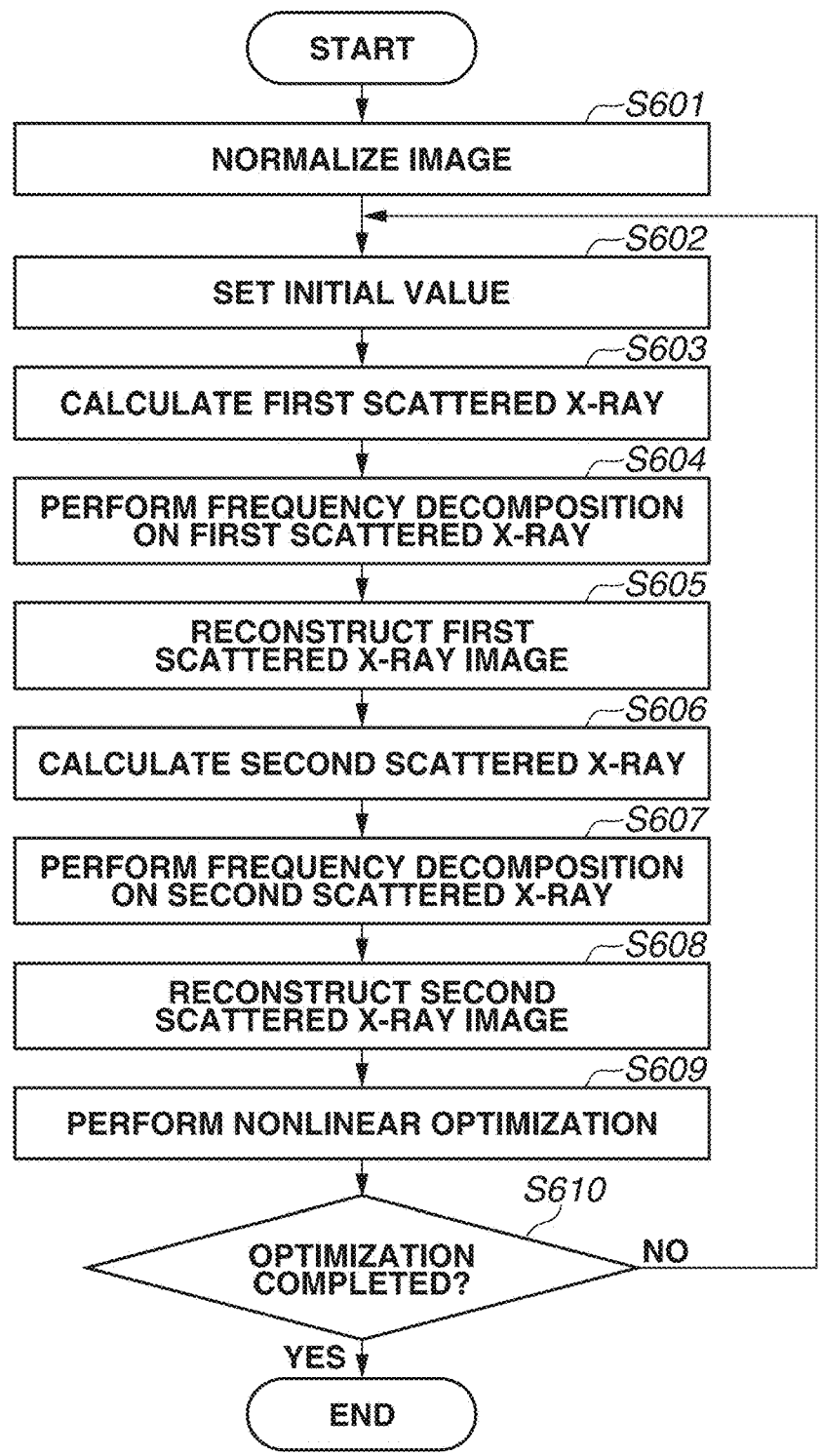
FIG. 6 is a flowchart illustrating processing according to another exemplary embodiment of the present invention.

FIG. 6 is a flowchart illustrating processing according to the another exemplary embodiment of the present invention. Steps S601, S602, S603, S606, S609, and S610 are similar to steps S301, S302, S303, S305, S307, and S308 illustrated in FIG. 3, respectively, and detailed descriptions thereof will be omitted.

In step S603, similar to step S303, the CPU 201 obtains the first output data.

In step S604, the frequency processing module 222 implemented by the CPU 201 performs multiple frequency decomposition processing on the first output data calculated in step S603. The present exemplary embodiment utilizes Laplacian pyramid decomposition which is a general-purpose high-speed technique. Other techniques for decomposing the data into frequency bands, such as fast Fourier transform and Wavelet decomposition, may be used.

FIG. 7A illustrates a concept of Laplacian pyramid decomposition. First output data $L_1$ calculated in step S603 is represented by $$L_1 = 1 - P(x,y) \tag{24}$$

A low-frequency component $L_2$ can be obtained in such a manner that aliasing processing is performed on the first output data $L_1$ using a two-dimensional low-pass filter AF illustrated in FIG. 7B and x1/2 downsampling is performed in the vertical and horizontal directions, as represented by $$L_2 = \downarrow AF * L_1 \tag{25},$$

where $\downarrow$ denotes x1/2 downsampling. A low-frequency component $L_n$ can be successively obtained in a similar way, as represented by $$L_n = \downarrow AF * L_{n-1} \tag{26}.$$

A high-frequency component $H_n$ can be obtained in such a manner that x2 upsampling is performed on a component $L_{n+1}$, aliasing processing is performed using a two-dimensional low-pass filter AF illustrated in FIG. 7B, and the result is subtracted from the component $L_n$, as represented by $$H_n = L_n - AF * \uparrow L_{n+1} \tag{27},$$

where $\uparrow$ denotes x2 upsampling. Successively performing processing represented by Formulas 15 and 16 enables decomposing the data into n different frequency bands and generating the components $L_n$ and $H_n$. Images of a plurality of frequency bands are generated in this way.

Figure 8:
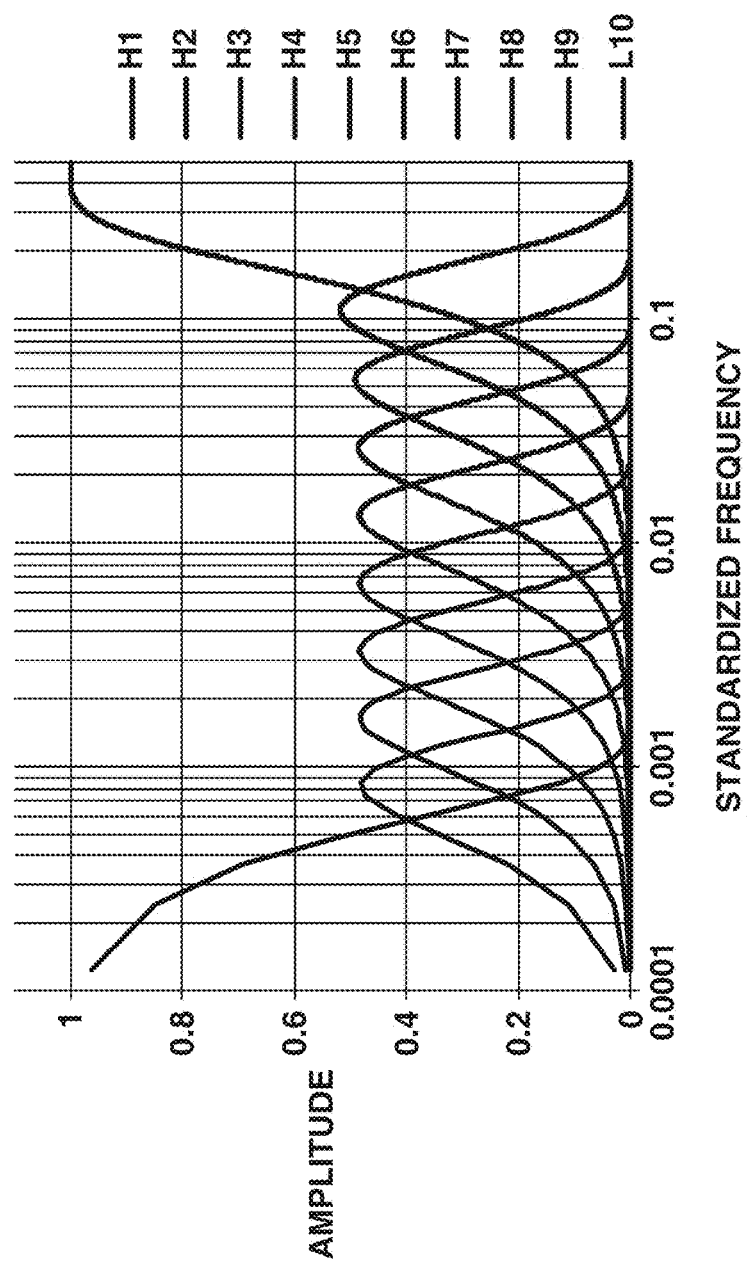
FIG. 8 is a diagram illustrating frequency characteristics of frequency decomposition based on Laplacian pyramid according to the another exemplary embodiment of the present invention.

FIG. 8 is a diagram illustrating frequency characteristics of frequency decomposition by Laplacian pyramid decomposition, more specifically, examples of frequency characteristics of the components $L_n$ and $H_n$ for each frequency band generated by Laplacian pyramid decomposition in step S604. For example, when an image having 1000 pixels in the horizontal and vertical directions is decomposed up into a component $L_{10}$, the component $L_{10}$ is decomposed to the level of several pixels in the horizontal and vertical directions. The high frequency component $H_n$ of each level is obtained by performing band limitation on the input component $L_1$.

In step S605, the frequency decomposition components $L_n$ and $H_n$ obtained by decomposing the first output data obtained in up to step S603 into a plurality of frequency bands in step S604 are reconstructed by the frequency processing module 222 implemented by the CPU 201. In this processing, as illustrated in FIG. 7C, the component $L_n$ can be reconstructed by performing x2 upsampling on the component $L_{n+1}$ for each level in the horizontal and vertical directions, performing aliasing processing using a low-pass filter AF illustrated in FIG. 7B, and adding the result to the component $H_n$. For example, when data is decomposed to the component $L_{10}$, an component $L_9'$ is represented by $$L'_9 = \alpha_9 H_9 + \alpha_{10} AF^* \uparrow L_{10} \qquad (28).$$

Therefore, an component $L'_n$ is represented by $$L'_n = \alpha_n H_n + AF^* \uparrow L'_{n+1} \qquad (29),$$

where $\alpha_n$ is an association constant. The frequency processing module 222 successively performs this calculation. In the present exemplary embodiment, a reconstructed component $L_1'$ is assumed to be the frequency component $S_1$ of the first output data. The frequency component $S_1$ can be represented by adjusting $\alpha_n$, and weighting and combining n frequency components.

In step S606, similar to step S305, the frequency processing module 222 obtains the second output data.

In step S607, similar to step S604, the frequency processing module 222 decomposes the second output data obtained in step S606 into a plurality of frequency decomposition components $L_n$ and $H_n$.

In step S608, similar to step S605, the frequency processing module 222 reconstructs the frequency decomposition components $L_n$ and $H_n$ obtained in step S607. More specifically, an component $L_9'$ is represented by $$L'_9 = \beta_9 H_9 + \beta_{10} AF^* \uparrow L_{10} \qquad (30)$$

and the component $L_n'$ is represented by $$L'_n = \beta_n H_n + AF^* \uparrow L_{n+1} \qquad (31).$$

where $\beta_n$ is an association constant. The frequency processing module 222 successively performs this calculation. In the present exemplary embodiment, the reconstructed component $L_1'$ is assumed to be the frequency component $S_2$ of the second output data. The frequency component $S_2$ can be represented by adjusting $\beta_n$, and weighting and combining n frequency components.

Also in the present exemplary embodiment, an approximation technique has specifically been described with reference to two models, the first and the second scattered X-ray models. The relevant technique approximates the total intensity of the scattered radiation resulting from the X-ray scattering on the path along which the radiation produced from the X-ray source 101 linearly reaches each radiation detecting element 102a providing the pixel value of the radiation image. However, as illustrated in Formulas (19) and (20), the assumption of the attenuation distance after scattering can be adjusted by parameters. Therefore, the present invention is not limited to the two models, and may include models approximated at different attenuation distances by suitably selecting suitable parameters. Using a weighted average filter as a low-pass filter enables expressing the spread centering on the periphery of the target pixel. Using a moving average filter as a low-pass filter enables expressing the spread up to a pixel distant from the target pixel.

In the present exemplary embodiment, the scattered radiation component can be expressed by a plurality of frequency components by adjusting $\alpha_n$ and $\beta_n$. At least either one of the first and the second output data may be decomposed into components of three or more frequency bands. By decomposing the data into components of three or more frequency bands, it is possible to estimate the low-frequency component scattered and widely spread in the body, and the structure of a portion where the X-ray absorption largely changes in the object 103, such as the skin line and the lung field, with higher accuracy.

The above-described scattered radiation models and modifications of functions grasped from various viewpoints can also be used in the present exemplary embodiment, and are included in the present invention.

The present exemplary embodiment performs fitting processing with a plurality of functions on a two-dimensional image obtained by radiation imaging to estimate the scattered radiation component. The present exemplary embodiment includes an example of applying the above-described scattered radiation component estimation processing to a tomography image. The present invention also include an example of applying the above-described scattered radiation component estimation processing on a radiation image obtained in what is called radiography (imaging by irradiating the object 103 with a radiation from one direction and using a two-dimensional detector). Since it is not necessary to extract a portion in which the absorption of radiation changes through analysis processing, such as segmentation, the scattered radiation component can be estimated through more robust processing.

Further, it is desirable to turn scattered radiation reduction processing ON and OFF according to the imaging target portion.

Figure 9A:
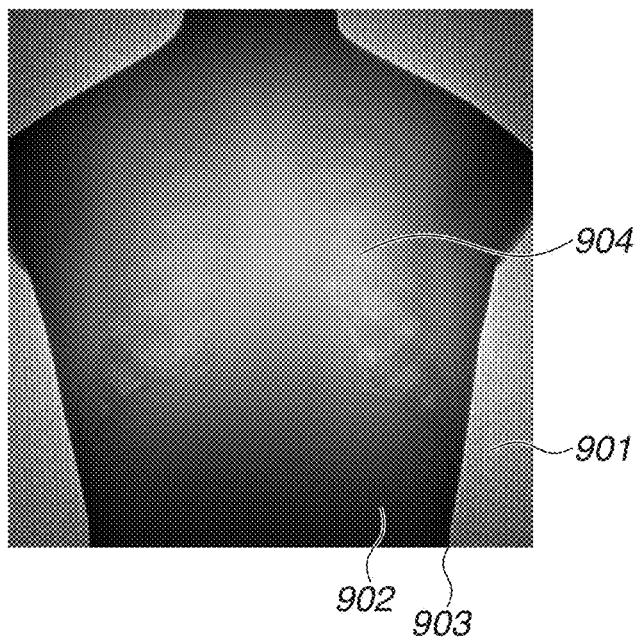
FIGS. 9A and 9B are diagrams illustrating examples of a scattered radiation component included in a radiation image measured by using a phantom.
Figure 9B:
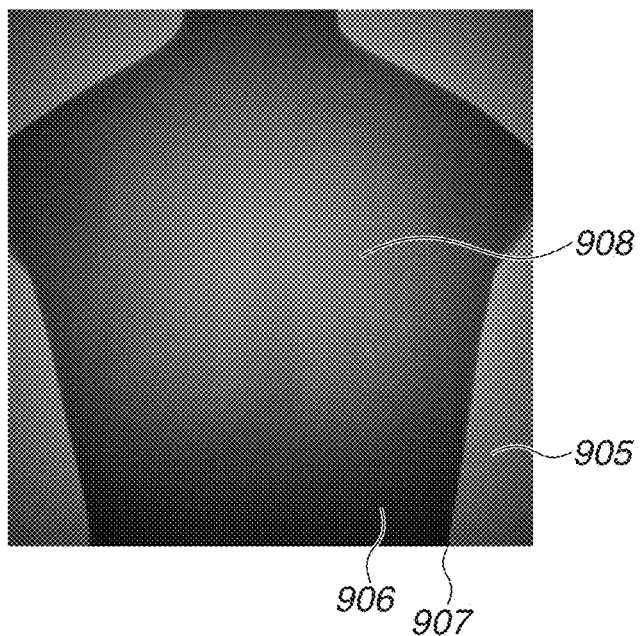

FIG. 9B is a diagram illustrating an example in which the scattered radiation component included in a radiation image acquired by using a thoracic phantom is obtained using the image processing according to the present invention. Similar to FIG. 9A illustrating the scattered radiation component acquired on an experimental basis, FIG. 9B illustrates the intensity distribution in a through-exposure region 905 and a lung field region 908, and a skin line 907.

Although the image processing apparatus 105 according to the above-described exemplary embodiment is a single apparatus, the present invention also includes an exemplary embodiment in which the above-described processing is performed by an image processing system in which apparatuses including a plurality of information processing apparatuses are combined and capable of communicating with each other. Alternatively, the above-described processing may be performed by a server apparatus or a server group common to a plurality of modalities. In this case, the common server apparatus corresponds to the image processing apparatus 105 according to the exemplary embodiment, and the server group corresponds to the image processing system according to the exemplary embodiment. A plurality of apparatuses constituting the information system 120 or the image processing system only needs to be capable of communicating with each other at a predetermined communication rate, and does not need to exist in the same facility or in the same country.

The present invention includes an exemplary embodiment in which software (program) for implementing the above-described functions is supplied to a system or apparatus, and a computer of the system or apparatus reads and executes the supplied program code.

Therefore, the program code itself installed in the computer to implement processing according to the present exemplary embodiment is also a part of the present invention. Further, an operating system (OS) operating on the computer may perform a part or whole of actual processing based on instructions included in the program read by the computer, and the functions of the above-described exemplary embodiments may also be implemented through the processing.

An exemplary embodiment suitably combining the above-described exemplary embodiments is also included in the present invention.

According to the present invention, it is possible to more correctly estimate the intensity distribution of the scattered radiation by performing estimation based on a first function corresponding to the intensity of the scattered radiation including a multiple-times scattered radiation resulting from a radiation scattering a plurality of times in an object and on a second function corresponding to the intensity of the single-time scattered radiation resulting from the radiation scattering once in the object.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments.

This application claims the benefit of Japanese Patent Application No. 2015-082094, filed Apr. 13, 2015, and No. 2015-132180, filed Jun. 30, 2015, which are hereby incorporated by reference herein in their entirety.

What is claimed is:

1. An image processing apparatus comprising:
a receiver configured to receive a radiation image obtained by irradiating an object with a radiation;
an image processor configured to estimate a scattered radiation component included in the radiation image received by the receiver, based on a specific frequency component of an output of a first function and a specific frequency component of an output of a second function, the first function corresponding to an intensity of a scattered radiation including a multiple-times scattered radiation which is a radiation scattered a plurality of times in the object and the second function corresponding to an intensity of a single-time scattered radiation which is a radiation scattered once in the object; and
a transmitter configured to transmit a corrected image obtained by reducing the scattered radiation component estimated by the image processor from the received radiation image.

2. The image processing apparatus according to claim 1, wherein the image processor is configured to weight and combine a specific frequency component of an output of the first function and a specific frequency component of an output of the second function to estimate the scattered radiation component.

3. The image processing apparatus according to claim 2, wherein the specific frequency component of the output of the first function and the specific frequency component of the output of the second function lie in mutually different frequency ranges.

4. The image processing apparatus according to claim 3, wherein the image processor is configured to decompose each of the outputs of the first and the second functions into a plurality of different frequency components, and to weight and combine the plurality of the different frequency components to estimate the scattered radiation component included in the received radiation image.

5. The image processing apparatus according to claim 4, wherein the plurality of the different frequency components is obtained by decomposing at least either one of the outputs of the first and the second functions into three or more frequency ranges.

6. The image processing apparatus according to claim 1, wherein the first function is a function of P and outputs a minimum value when P is a maximum value, and outputs a positive value when P is a minimum value, and is converged to a positive value as P comes close to the minimum value, where P is a variable related to a intensity of a primary radiation which is a radiation having traveled straight from a radiation generating apparatus to a radiation detecting element for providing a pixel value of the received radiation image.

7. The image processing apparatus according to claim 1, wherein the first function is a function of P and outputs a minimum value when P is a maximum value, and monotonically decreases in a range of P, where P is a variable related to a intensity of a primary radiation which is a radiation having traveled straight from a radiation generating apparatus to a radiation detecting element for providing a pixel value of the received radiation image.

8. The image processing apparatus according to claim 1, wherein the first function is based on an assumption that a scattered radiation is not attenuated.

9. The image processing apparatus according to claim 1, wherein the image processor is configured to normalize a pixel value of the received radiation image with a value corresponding to an incident dose to the object, and
wherein the first function is represented by an approximation formula 1-P where P corresponds to a primary radiation component in the normalized radiation image.

10. The image processing apparatus according to claim 9, wherein the image processor is configured to normalize a pixel value of the radiation image with a value corresponding to an incident dose to the object, and
wherein the second function is represented by an approximation formula $-P\ln P$ where P corresponds to a primary radiation component in the normalized radiation image.

11. The image processing apparatus according to claim 1, wherein the second function is a function of P and outputs a minimum value when P is a maximum value, and outputs a positive value when P is neither a maximum value nor a minimum value, where P is a variable related to a intensity of a primary radiation which is a radiation having traveled straight from a radiation generating apparatus to a radiation detecting element for providing a pixel value of the received radiation image.

12. The image processing apparatus according to claim 1, wherein the second function is a function of P and outputs a minimum value when P is a maximum value or a minimum value, and outputs a positive value when P is neither a maximum value nor a minimum value, and is a local maximum value in a range of P, where P is a variable related a intensity of a primary radiation which is a radiation having traveled straight from a radiation generating apparatus to a radiation detecting element for providing a pixel value of the received radiation image.

13. The image processing apparatus according to claim 1, wherein the second function is based on an assumption that a scattered radiation is further attenuated in the object.

14. The image processing apparatus according to claim 1, wherein the image processor is configured to normalize a pixel value of the radiation image with a value corresponding to an incident dose to the object, and
wherein the second function is represented by an approximation formula $-P\ln P$ where P corresponds to a primary radiation component in the normalized radiation image.

15. The image processing apparatus according to claim 1, wherein a plurality of different frequency components is obtained by decomposing each of the outputs of the first and the second functions into two different frequency components, and
wherein the image processor is configured to estimate the scattered radiation component included in the radiation image by weighting and combining the two different frequency components.

16. The image processing apparatus according to claim 15, wherein the image processor is configured to weight more a frequency component on a lower frequency side among the two different frequency components than the other frequency component and then to combine weighted two different frequency components, to estimate the scattered radiation component included in the received radiation image.

17. The image processing apparatus according to claim 1, wherein the first function is a function of P and is a function in which a derived function outputs a negative value when P is a minimum value, and
wherein the second function is a function of P and is a function in which a derived function has a positive value when P is a minimum value,
where P is a variable related a intensity of a primary radiation which is a radiation having traveled straight from a radiation generating apparatus to a radiation detecting element for providing a pixel value of the received radiation image.

18. The image processing apparatus according to claim 1, wherein the receiver and the transmitter are communication circuits.

19. The image processing apparatus according to claim 1, further comprising:
a setting unit configured to set a parameter for the combination by using imaging conditions including at least one of a tube current of a radiation generating apparatus, an irradiation duration of the radiation generating apparatus, and an imaging target portion.

20. The image processing apparatus according to claim 1, wherein the image processor is configured to obtain the scattered radiation component of the received radiation image as an output by combining the specific frequency component of the output from the first function input the primary radiation component and the specific frequency component of the output from the second function input the primary radiation component, and
wherein, on an assumption that a sum total of the primary radiation component and the scattered radiation component of the received radiation image coincides with the received radiation image, the image processor is configured to input the received radiation image and derive the scattered radiation component of the received radiation image using a successive approximation method.

21. The image processing apparatus according to claim 20, wherein a maximum likelihood estimation method is used as the successive approximation method.

22. The image processing apparatus according to claim 1, wherein the receiver is configured to receive a radiation image captured by irradiating the object with a radiation from one direction.

23. The image processing apparatus according to claim 1, wherein the receiver is configured to receive in advance a reduced image of a radiation image having a smaller data amount than the radiation image from a radiation detector for obtaining the radiation image, and completes reception of the radiation image,
wherein the image processor estimates the scattered radiation component of the radiation image based on the received reduced image, and
wherein the transmitter outputs a corrected image obtained by reducing the scattered radiation component from the received radiation image.

24. The image processing apparatus according to claim 1, wherein the transmitter is configured to output a DICOM image file including the corrected image and DX or RF associated with the corrected image as a Modality tag.

25. An image processing apparatus comprising:
a receiver configured to receive a radiation image obtained by irradiating an object with a radiation;
an image processor configured to estimate a scattered radiation component included in the received radiation image by weighting and combining at least two frequency components obtained by decomposing an output of a function specific to the radiation image into a plurality of frequency components; and
a transmitter configured to output a corrected image obtained by reducing the scattered radiation component estimated by the image processor from the received radiation image.

26. An image processing process comprising the steps of:
acquiring a radiation image obtained by irradiating an object with a radiation;
estimating a scattered radiation component included in the received radiation image, based on a specific frequency component of an output of a first function and a specific frequency component of an output of a second function, wherein the first function corresponds to an intensity of a scattered radiation which is a radiation scattered a plurality of times in the object, and the second function corresponds to an intensity of a single-time scattered radiation which is a radiation scattered once in the object; and outputting a corrected image obtained by reducing the scattered radiation component from the received radiation image.

27. A non-transitory recording medium storing a program for causing a computer to execute a process comprising:
image acquisition processing configured to acquire a radiation image obtained by irradiating an object with a radiation;
estimation processing configured to estimate a scattered radiation component included in the received radiation image, based on a specific frequency component of an output of a first function and an output of a second function, wherein the first function corresponds to an intensity of a scattered radiation including a multiple-times scattered radiation which is a radiation scattered a plurality of times in the object, and the second function corresponds to an intensity of a single-time scattered radiation which is a radiation scattered once in the object; and
output processing configured to output a corrected image obtained by reducing the scattered radiation component from the received radiation image.

28. An image processing apparatus comprising:
a receiver configured to receive a radiation image obtained by irradiating an object with a radiation from a radiation generating apparatus;
an image processor configured to estimate a scattered radiation component and a primary radiation component included in the radiation image,
wherein the image processor approximates an intensity of a scattered radiation which is a radiation scattered on a path from the radiation generating apparatus to a radiation detecting element for providing a pixel value of the radiation image, for a path by using a plurality of scattered radiation models, corresponding to different attenuation distances on the path, based on an assumption that the scattered radiation is further attenuated in the object after scattering, and further performs the approximation on the pixel value corresponding to an output from the radiation detecting element to estimate the scattered radiation component and the primary radiation component; and
a transmitter configured to transmit a corrected image obtained by reducing the scattered radiation component estimated by the image processor from the received radiation image.

29. An image processing method comprising steps of:
acquiring a radiation image obtained by irradiating an object with a radiation from a radiation generating apparatus;
estimating a scattered radiation component and a primary radiation component included in the acquired radiation image,
approximating an intensity of a scattered radiation, which is a radiation scattered on a path from the radiation generating apparatus to a radiation detecting element for providing a pixel value of the acquired radiation image, for a path by using a plurality of scattered radiation models, corresponding to different attenuation distances on the path, based on an assumption that the scattered radiation is further attenuated in the object after scattering,
performing the approximation on the pixel value corresponding to an output from the radiation detecting element to estimate the scattered radiation component and the primary radiation component; and
transmitting a corrected image based on the primary radiation component.

* * * * *